United States Patent [19]

Bachman et al.

[11] Patent Number: 4,515,731
[45] Date of Patent: May 7, 1985

[54] ASYMMETRIC CATALYSIS

[75] Inventors: Gerald L. Bachman, Des Peres; Billy D. Vineyard, St. Louis, both of Mo.

[73] Assignee: Monsanto Company, St. Louis, Mo.

[21] Appl. No.: 512,282

[22] Filed: Jul. 8, 1983

Related U.S. Application Data

[63] Continuation of Ser. No. 274,976, Jun. 18, 1981, abandoned, which is a continuation-in-part of Ser. No. 854,447, Nov. 23, 1977, abandoned, which is a continuation of Ser. No. 607,304, Aug. 25, 1975, abandoned.

[51] Int. Cl.$^3$ ............................................. C07C 121/78
[52] U.S. Cl. ............................... 260/465 D; 260/465.4; 560/24; 560/757
[58] Field of Search ................... 260/465 D, 465.4; 560/24, 157

[56] References Cited

U.S. PATENT DOCUMENTS 4,008,281  2/1977  Knowles et al. ............ 260/465 D X

FOREIGN PATENT DOCUMENTS 822848  12/1974  Belgium .

OTHER PUBLICATIONS

Vineyard et al., J.A.C.S., vol. 99, 5946, (1977).
Morrison et al., J.A.C.S., vol. 93, 1301, (1971).
Kagan et al., J. Organometallic Chem., vol. 90, 353, (1975).

*Primary Examiner*—Dolph H. Torrence
*Attorney, Agent, or Firm*—J. H. Beusen; J. C. Logomasini; A. H. Cole

[57] ABSTRACT

Catalytic asymmetric hydrogenation of the Z geometric isomer of a compound of the formula

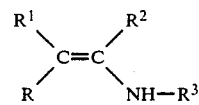

wherein at least one of R and $R^1$ represents hydrogen and the other represents hydrogen, lower alkyl or aryl; $R^2$ represents

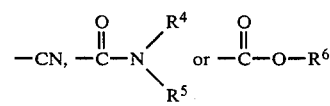

wherein $R^4$ and $R^5$ each independently represent hydrogen, lower alkyl or aryl, $R^6$ represents hydrogen, lower alkyl, aryl or an alkali metal; and $R^3$ represents

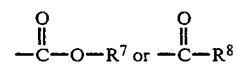

wherein $R^7$ and $R^8$ each independently represent lower alkyl or aryl; provided that, when $R^3$ is

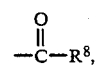

$R^2$ is —CN, in the presence of a homogeneous, coordination complex catalyst comprising rhodium, iridium or ruthenium in combination with an optically active bis phosphine ligand provides an outstanding level of optical purity.

20 Claims, No Drawings

ASYMMETRIC CATALYSIS

This is a continuation of application Ser. No. 274,976 filed June 18, 1981 abandoned which was a continuation-in-part of application Ser. No. 854,447 filed Nov. 23, 1977 abandoned, which was a continuation of application Ser. No. 607,304 filed Aug. 25, 1975 abandoned.

This invention relates to new catalytic asymmetric hydrogenation processes. More specifically, this invention is directed to a hydrogenation process which provides outstanding levels of optical purity.

Homogeneous catalysis, i.e., those catalyzed reactions that are conducted where both reactants and catalysts are soluble in the reaction mass, have been found to be particularly useful in processes wherein an asymmetric result is obtained. For instance, it has been found that when an olefin, which is capable of forming a racemic mixture is hydrogenated in the presence of a homogeneous, optically active catalyst, one or the other of the possible optical enantiomorphs is obtained in a major amount with the other optical enantiomorph being obtained in minor amounts. Furthermore, it has been found that certain such olefinic substrates, for instance, precursors of α-amino acids containing α-acylamido and carboxylic acids, salts, esters or amides substituents, are particularly amenable to hydrogenation with homogeneous, optically active catalysts. Such catalytic asymmetric hydrogenation processes have resulted in the production of large amounts of the desired optical enantiomorph. It has more recently been found that certain homogeneous, optically active catalysts containing optically active bis phosphine ligands provide outstanding levels of optical purity, i.e., reaching 80% and higher with such α-amino acid precursors. Other olefinic substrates which would provide such outstanding levels of optical purity of optical enantiomorphs leading to α-amino acids, upon hydrogenation, are particularly desirable.

It is an object of the present invention to provide such olefinic substrates.

It is a further object to provide novel catalytic asymmetric hydrogenation processes which produce large amounts of the desired optical enantiomorph.

These and other objects, aspects and advantages of this invention will become apparent from a consideration of the accompanying specification and claims.

SUMMARY OF THE INVENTION

In accordance with the above objects, the present invention provides catalytic asymmetric hydrogenation of the Z geometric isomer of a compound of the formula

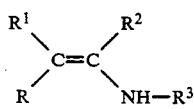

wherein at least one of R and $R^1$ represents hydrogen and the other represents hydrogen, lower alkyl or aryl; $R^2$ represents

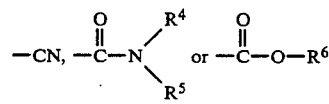

wherein $R^4$ and $R^5$ each independently represent hydrogen, lower alkyl or aryl, $R^6$ represents hydrogen, lower alkyl, aryl or an alkali metal; and $R^3$ represents

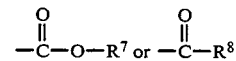

wherein $R^7$ and $R^8$ each independently represent lower alkyl or aryl; provided that, when $R^3$ is

$R^2$ is —CN, in the presence of a homogeneous, coordination complex catalyst comprising rhodium, iridium or ruthenium in combination with an optically active bis phosphine ligand. This process provides outstanding levels of optical purity of desired optical enantiomorphs.

DESCRIPTION OF THE PREFERRED EMBODIMENTS

The hydrogenation reaction is illustrated by the following equation:

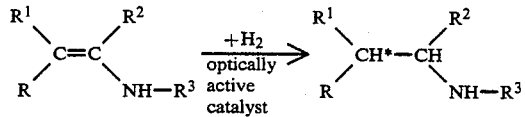

*shows one or both carbon atoms are asymmetric wherein R, $R^1$, $R^2$ and $R^3$ have the same meaning as described above It has been found that the geometric stereochemistry of the olefinic substrate being hydrogenated effects the results obtained. In general, it is necessary to utilize the Z geometric isomer to realize the outstanding levels of optical purity with the olefinic substrates of this invention. The E and Z geometric isomer nomenclature is described in detail in The Journal of Organic Chemistry, Vol. 35, No. 9, September 1970, pp 2849–2867. It has been found that either the E or Z geometric isomer will, upon hydrogenation, produce the same optical enantiomorph when using the same catalyst but at different levels of optical purity.

R, $R^1$, $R^4$ and $R^5$ are each independently exemplified by hydrogen, lower alkyl groups (e.g. methyl, ethyl, propyl, butyl, amyl) and by aryl groups such as phenyl. The alkyl and phenyl groups may be unsubstituted or they may be substituted by a large number of groups and such substituents are limited only by the desired make-up of the optical enantiomorph that is the desired end-product. Exemplary substituent groups may include methyl, ethyl, methoxy and acetoxy.

$R^6$ is exemplified by hydrogen, lower alkyl, aryl as described above or alkali metal groups such as sodium, potassium or lithium.

$R^7$ and $R^8$ are independently exemplified by lower alkyl or aryl groups as described above.

As described above, the alkyl or aryl groups may be substituted by a large variety of groups. Further, it may be that such substituent groups may be precursors of desired substituents. Thus, if the desired substituent on the saturated end-product is hydroxyl, the substituent on the unsaturated substrate might be

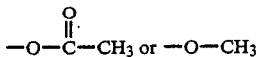

which would provide the hydroxyl group by simple hydrolysis after the catalytic asymmetric hydrogenation.

The optical enantiomorphs resulting from the process of this invention are particularly desirable in that optical activity is a desirable characteristic of α-amino acids, i.e. normally only one or the other optical enantiomorphs is useful in living organisms. For instance, those optical enantiomorphs of α-amino acids resulting from this process which have phenyl or substituted phenyl substituents on the β position lead to desirable L-phenylalanines.

The compounds represented by the following structural formula provide excellent results with the process of this invention and therefore represent compounds particularly amenable to the hydrogenation process of this invention

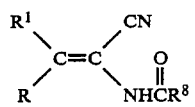

wherein R and R¹ have the same meaning as described above.

Particularly preferred embodiments of this invention are the catalytic asymmetric hydrogenation of (Z)-ethyl-2-(N-ethoxycarbonylamino)-3-phenyl-2-propenoate (Compound I, below. Note, also, Example 1) and (Z)-2-benzamido-3-phenyl-2-propenenitrile (Compound II, below. Note, also, Example 4).

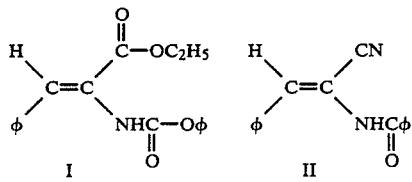

The L enantiomorph of phenylalanine can be readily derived from such procedures.

Such hydrogenation reactions are usually conducted in a solvent, such as benzene, ethanol, 2-propanol, toluene, cyclohexane, and mixtures of these solvents. Almost any aromatic or saturated alkane or cycloalkane solvent, which is inactive to the hydrogenation conditions of this reaction, can be used. The preferred solvents are alcohols particularly methanol, ethanol and 2-propanol.

The homogeneous, optically active catalysts useful in this invention are soluble coordination complexes comprising a metal which is rhodium, iridium or ruthenium in combination with at least one optically active bis phosphine ligand, preferably at least about 0.5 moles of bis phosphine ligand per mole of metal. These catalysts are soluble in the reaction mass and are therefore referred to as "homogeneous" catalysts.

These catalysts contain optically active bis phosphine compounds of general formulae I and II below. These bis phosphine compounds are characterized by the structural formula

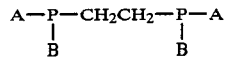

wherein A and B each independently represent substituted and unsubstituted alkyl of from 1 to 12 carbon atoms, substituted and unsubstituted cycloalkyl having from 4 to 7 carbon atoms, substituted and unsubstituted aryl; provided that such substituents provide no significant interference with the steric requirements around the phosphorus atom and A and B are different.

Among such bis phosphine compounds, those having two dissimilar aryl groups on each phosphorus atom are also preferred, particularly those wherein one such aryl group has an alkoxy substituent at the ortho position.

More preferred bis phosphine compounds useful in the present invention are the optically active bis phosphines characterized by the structural formula

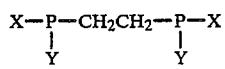

wherein

X represents substituted and unsubstituted phenyl,
Y represents substituted and unsubstituted 2-alkoxyphenyl wherein the alkoxy has from 1 to 6 carbon atoms; provided that such substituents provide no significant interference with the steric requirements around the phosphorus atom and X and Y are different.

The catalysts prepared utilizing those optically active bis phosphine compounds of more specific formula III, below, are more particularly preferred in the catalytic asymmetric hydrogenation reactions of this invention.

Still more particularly preferred optically active bis phosphine compounds useful in the present invention are characterized by the structural formula

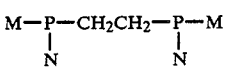

wherein
M represents

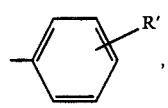

N represents

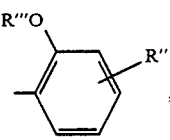

R' and R'' each independently represent hydrogen, halogen, alkyl having from 1 to 6 carbon atoms and alkoxy having from 1 to 6 carbon atoms, and R‴ represents normal alkyl having from 1 to 6 carbon atoms;

provided that M and N are different.

A particularly preferred optically active bis phosphine compound useful in the present invention is 1,2-bis(o-anisylphenylphosphino) ethane.

Other exemplary optically active bis phosphine compounds useful in this invention are:

1,2-bis(o-anisyl-4-methylphenylphosphino) ethane
1,2-bis(o-anisyl-4-chlorophenylphosphino) ethane
1,2-bis(o-anisyl-3-chlorophenylphosphino) ethane
1,2-bis(o-anisyl-4-bromophenylphosphino) ethane
1,2-bis[(2-methoxy-5-chlorophenyl)-phenylphosphino] ethane
1,2-bis[(2-methoxy-5-bromophenyl)-phenylphosphino] ethane
1,2-bis(2-ethoxyphenylphenylphosphino) ethane
1,2-bis[o-anisyl-(p-phenylphenyl)phosphino] ethane
1,2-bis[(2-methoxy-4-methylphenyl)-phenylphosphino] ethane
1,2-bis(2-ethoxyphenyl-4-chlorophenylphosphino) ethane
1,2-bis(o-anisyl-2-methylphenylphosphino) ethane
1,2-bis(o-anisyl-4-ethylphenylphosphino) ethane
1,2-bis(o-anisyl-3-ethylphenylphosphino) ethane
1,2-bis(o-anisyl-3-phenylphenylphosphino) ethane For these bis phosphine compounds to be useful in asymmetric hydrogenation reactions they must be utilized as the optically active enantiomorph and not in the meso form.

Optically activity of the coordinated complex catalysts useful in this invention resides in the bis phosphine ligand. This optical activity results from having two different groups, in addition to the ethane bridge, on the phosphorus atom.

Illustrative coordination metal complexes can be represented by the formula MeTL wherein Me is a transition metal selected from the group consisting of rhodium, iridium and ruthenium; T is selected from the group consisting of hydrogen, fluorine, bromine, chlorine and iodine; L is the optically active bis phosphine ligand as previously defined.

It has been found that outstanding levels of optical purity of the desired optical enantiomorphs can be achieved not only with the above-described catalysts represented by the formula MeTL, which are coordination complexes of a metal selected from the group consisting of rhodium, iridium and ruthenium, but can also be achieved when the hydrogenation is carried out in the presence of an in situ complex catalyst that comprises a solution of a transition metal selected from the group consisting of rhodium, iridium and ruthenium and at least about 0.5 moles of the optically active bis phosphine ligand per mole of metal. For instance, such catalysts can be prepared by dissolving a soluble compound of the appropriate metal in a suitable solvent together with an optically active bis phosphine compound as the ligand wherein the ratio of ligand to metal is at least 0.5 moles of ligand per mole of metal, preferably one mole of ligand per mole of metal. It has been found that the catalyst is formed in situ by adding a soluble metal compound to the reaction mass together with the addition of the proper amount of the optically active bis phosphine ligand to the reaction mass either before or during hydrogenation.

The preferred metal for use in this process is rhodium. Soluble rhodium compounds that can be utilized include rhodium trichloride hydrate, rhodium tribromide hydrate, rhodium sulfate, organic rhodium complexes with ethylene, propylene, etc., and bis olefins such a 1,5-cyclooctadiene and 1,5-hexadiene, bicyclo-2.2.1-hepta-2,5-diene and other dienes which can form bidentate ligands, or an active form of metallic rhodium that is readily solubilized.

It has been found that a preferred embodiment of this invention is the hydrogenation process where the optically active bis phosphine ligand is present in a ratio of about 0.5 to about 2.0, preferably, 1.0, moles of bis phosphine ligand per mole of metal. In practice, it is preferred to have the optically active catalyst in a solid form for purposes of handling and storage. It has been found that outstanding results can be obtained with solid, cationic coordination metal complexes.

Cationic coordination metal complexes containing one mole of the optically active bis phosphine ligand per mole of metal and a chelating bis olefin represent a preferred form of the catalysts useful in the present invention. For instance, using organic rhodium complexes, as described above, one can prepare such cationic coordination rhodium complexes by slurrying the organic rhodium complex in an alcohol, such as ethanol, adding one mole per mole of rhodium of the optically active bis phosphine compound so that an ionic solution is formed, followed by the addition of a suitable anion, such as, for instance, tetrafluoroborate, tetraphenylborate or any other anion that will result in the precipitation or crystallization of a solid, cationic coordination metal complex either directly from the solvent or upon treatment in an appropriate solvent.

Exemplary cationic coordination metal complexes are cyclooctadiene-1,5-[1,2-bis(o-anisylphenylphosphino) ethane] rhodium tetrafluoroborate, cyclooctadiene-1,5-[1,2-bis(o-anisylphenylphosphino) ethane] rhodium tetraphenylborate and bicyclo-2.2.1-hepta-2,5-diene-[1,2-bis(o-anisylphenylphosphino) ethane] rhodium tetrafluoroborate.

Without prejudice to the present invention it is thought that the catalyst is present actually as a catalyst precursor and that upon contact with hydrogen the catalyst is converted to an active form. This conversion can, of course be carried out during the actual hydrogenation or can be accomplished by subjecting the catalyst (or precursor) to hydrogen prior to addition to the reaction mass to be hydrogenated.

As previously noted, the catalyst can be added to the solvent either as a compound per se or as its components which then form the catalyst in situ. When the catalyst is added as its components it may be added prior to or after the addition of the olefinic substrate. Components for the preparation of the catalyst in situ are the soluble metal compound and the optically active bis phosphine compound. The catalyst can be added in any effective catalytic amount and generally in the range of about 0.001% to about 5% by weight of contained metal based on the olefinic substrate to be hydrogenated.

Within the practical limits, means should be provided so as to avoid contacting the catalyst or reaction mass with oxidizing materials. In particular, care should be taken so as to avoid contact with oxygen. It is preferred to carry out the hydrogenation reaction preparation and actual reaction in gases (other than $H_2$) that are inert to both reactants and catalysts such as, for instance, nitrogen or argon.

After addition of the reactants and catalyst to the solvent, hydrogen is added to the mixture until about 0.5 to about 5 times the mole quantity of the olefinic substrate present has been added. The pressure of the system will necessarily vary since it will be dependent upon the type of reactant, type of catalyst, size of hydrogenation apparatus, amount of reactants and catalyst and amount of solvent. Lower pressures, including atmospheric and sub-atmospheric pressure can be used as well as higher pressure.

Reaction temperatures may be in the range of about −20° C. to about 110° C. Higher temperatures may be used but are normally not required and may lead to an increase of side reactions.

Upon completion of the reaction which, is determined by conventional means, the product is recovered by conventional means.

Many naturally occurring products and medicaments exist in an optically active form. In these cases only the L or D form is usually effective. Synthetic preparation of these compounds in the past has required an additional step of separating the products into its enantiomorphs. This process is expensive and time consuming. This process of the present invention permits the direct formation of desired optical enantiomorphs with outstanding optical purity thus eliminating much of the time consuming and expensive separation of such optical enantiomorphs. Furthermore, the process provides a higher yield of the desired optical enantiomorph while concurrently decreasing the yield of the unwanted optical enantiomorph.

The hydrogenation process of this invention is particularly desirable because of its ability to not only provide an unusually high optical purity of the desired optical enantiomorph but also because of its ability to afford a rapid rate of hydrogenation at low catalyst concentrations.

The following examples will serve to illustrate certain specific embodiments within the scope of this invention and are not to be construed as limiting the scope thereof. In the examples, the percent optical purity is determined by the following equation (it being understood that the optical activity, expressed as specific rotation, is measured in the same solvent):

$$\% \text{ Optical Purity} = \frac{\text{Observed optical activity of the mixture} \times 100}{\text{Optical activity of pure optical isomer.}}$$

EXAMPLE 1

Preparation of
(Z)-ethyl-2-(N-ethoxycarbonylamino)-3-phenyl-2-propenoate

To a solution of 21.0 g. (0.12 mole) of ethyl N-(ethoxycarbonyl) glycine, 10.08 g. (0.096 mole) of benzaldehyde and 200 ml. of ethyl either, maintained at 5° C., was added 3.0 g. (0.13 mole) of sodium metal. The mixture was stirred 18 hours at ambient temperature and was filtered to remove the solid precipitate. The ethereal filtrate was washed with water and dried. The ether was stripped and the solid residue was recrystallized from toluene. The yield was 4.9 g., m.p. 102–107. The product was identified as (Z)-ethyl-2-(N-ethoxycarbonylamino)-3-phenyl-2-propenoate by NMR, GLC, and UV analysis.

EXAMPLE 2

Preparation of
ethyl-2-(N-ethoxycarbonylamino)-3-phenylpropanoate

A solution 2.29 g. of (Z)-ethyl-2-(N-ethoxycarbonylamino)-3-phenyl-2-propenoate, 0.0105 g. of cyclooctadiene-1,5-[1,2-bis(o-anisylphenylphosphino) ethane] rhodium tetrafluoroborate and 30 cc. of ethanol was hydrogenated at 3 atm. and 50° C. After 2½ hours, the solution was stripped on a rotary evaporator. NMR analysis indicated that hydrogenation was complete.

The hydrogenation product, ethyl-2-(N-ethoxycarbonylamino)-3-phenylpropanoate, was hydrolyzed to phenylalanine (with the L enantiomorph in major amount) in the following manner: To a solution of the residue from the above stripping in 30 cc. of acetic acid at 75° C., hydrogen bromide gas was slowly bubbled in the resulting solution for 1 hour. After holding for several hours, the acetic acid was removed on a rotary evaporator. The resulting residue was added to 25 cc. of water containing 2 cc. of 48% aqueous hydrogen bromide. The mixture was heated at reflux for 3½ hours, cooled to 25° C. and extracted with chloroform to remove non-hydrolyzed organics. The water solution, containing the phenylalanine hydrobromide salt and 1 cc. of added acetic acid was neutralized to pH 3 with a 50% NaOH solution. The optical rotation of the neutralized solution (100 cc.), containing the phenylalanine was determined with a polarimeter. $[\alpha]_D^{20} = -27.95°$ (C=1 in water), optical purity equals 88.7%.

EXAMPLE 3

Preparation of N-benzamidoacetonitrile

Sodium carbonate (0.108 mole) was added to a solution containing 20 g. of aminoacetonitrile hydrochloride (0.216 mole) in 150 cc. of water. The solution was cooled to 5° C. and 18.1 g. (0.216 mole) of sodium bicarbonate was added. 30.4 g. of benzoyl chloride (0.216 mole) was added dropwise over about 1½ hours to the cold aqueous solution and a solid formed. The resulting mass was allowed to warm to 20° C.; the solid was collected and washed thoroughly with water. The dry weight of the recovered material, which was crude N-benzamidoacetonitrile, was 33 g. (96% yield) m.p. 137°–139° C. This material was recrystallized from 100 cc. of methanol and 29 g. was recovered.

EXAMPLE 4

Preparation of
(Z)-2-benzamido-3-phenyl-2-propenenitrile

Hydrogen chloride gas was bubbled into a solution containing 4 g. of benzaldehyde (0.037 mole) and 6 g. of N-benzamidoacetonitrile (0.037 mole) in 100 cc. of diethyl ether maintained at 0°–5° C. Upon holding for about 1½ hours a solid precipitates 10.4 g. of this solid was collected by filtration.

The 10.4 g. of the solid collected above was added to a solution of 4 g. of sodium carbonate in 100 cc. of cold (0°–5° C.) water. The mixture was stirred for 1 hour at 5° C., then 10 cc. of acetone was added and the resulting mass allowed to warm to 20° C. The product, which was crude (Z)-2-benzamido-3-phenyl-2-propenenitrile (NMR), was collected and washed with water. The dry weight of collected material was 8.5 g. (92% yield). The 8.5 g. of this material was crystallized from 85 cc. of ethanol. Recovery was 6.8 g., m.p. 164°–165°.

EXAMPLE 5

Preparation of 2-benzamido-3-phenylpropanenitrile (A) A solution of 0.9956 g. of (Z)-2-benzamido-3-phenyl-2-propenenitrile, 0.0046 g. of cyclooctadiene-1,5-[1,2-bis(o-anisylphenylphosphino) ethane] rhodium tetrafluoroborate and 0.5 cc. of acetic acid in 30 cc. of methanol was hydrogenated in a Hoke bomb at 27 atm. and 50° C. Hydrogenation was complete in 3 hours. The solution was diluted to 200 cc. with methanol, observed rotation = $-0.359°$, $[\alpha]_D^{20} = -72.1°$. The pure enantiomorph of 2-benzamido-3-phenylpropanenitrile in a solution of comparable composition has a $[\alpha]_D^{20} = -84.3°$. Therefore, the optical purity was 85.5%.

(B) A solution of 0.9924 g. of (Z)-2-benzamido-3-phenyl-2-propenenitrile, 0.0153 g. of cyclooctadiene-1,5-[1,2-bis(o-anisylphenylphosphino) ethane] rhodium tetrafluoroborate and 2 drops of acetic acid in 30 cc. of methanol was subjected to 3 atm. of hydrogen pressure at 50° C. After about 24 hours, the solution was diluted to 200 cc. with methanol. The observed rotation was $-0.372°$, $[\alpha]_D^{20} = -75°$. Therefore, the optical purity was 89%.

While the invention has been described herein with regard to certain specific embodiments, it is not so limited. It is to be understood that variations and modifications thereof may be made by those skilled in the art without departing from the spirit and scope of the invention.

The embodiments of this invention in which a particular property or privilege is claimed are defined as follows:

1. An asymmetric hydrogenation process comprising hydrogenating an olefinic substrate consisting essentially of the Z geometric isomer of a compound of the formula

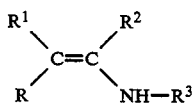

wherein at least one of R and $R^1$ represents hydrogen and the other independently represents hydrogen, unsubstituted or substituted lower alkyl or aryl; $R^2$ represents

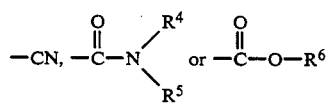

wherein $R^4$ and $R^5$ each independently represent hydrogen, unsubstituted or substituted lower alkyl or unsubstituted or substituted aryl, $R^6$ represents hydrogen, unsubstituted or substituted lower alkyl or unsubstituted or substituted aryl; and $R^3$ represents

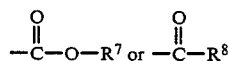

wherein $R^7$ and $R^8$ each independently represent unsubstituted or substituted lower alkyl or unsubstituted or substituted aryl; provided that when $R^3$ represents

$R^2$ represents —CN, in the presence of a catalytic amount of a homogeneous, coodination complex of rhodium, iridium or ruthenium in combination with an optically active bis phosphine ligand represented by the formula

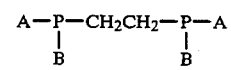

wherein A and B each independently represent substituted and unsubstituted alkyl of from 1 to 12 carbon atoms, substituted and unsubstituted cycloalkyl having from 4 to 7 carbon atoms, substituted and unsubstituted aryl; provided that such substituents provide no significant interference with the steric requirements around the phosphorus atom and A and B are different.

2. A hydrogenation process according to claim 1 wherein the bis phosphine ligand is represented by the formula

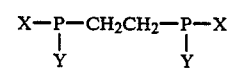

wherein
X represents substituted and unsubstituted phenyl,
Y represents substituted and unsubstituted 2-alkoxyphenyl wherein the alkoxy has from 1 to 6 carbon atoms; provided that such substituents provide no significant interference with the steric requirements around the phosphorus atom and X and Y are different.

3. A hydrogenation process according to claim 1 wherein the bis phosphine ligand is represented by the formula

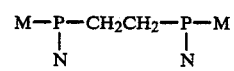

wherein
M represents

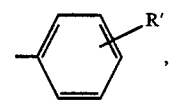

N represents

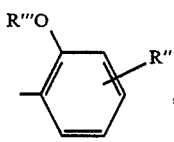

R' and R" each independently represent hydrogen, halogen, alkyl having from 1 to 6 carbon atoms and alkoxy having from 1 to 6 carbon atoms, and
R'" represents normal alkyl having from 1 to 6 carbon atoms;
provided that M and N are different.

4. A hydrogenation process according to claim 1 wherein the bis phosphine ligand is 1,2-bis(o-anisyl-penylphosphino) ethane.

5. A process according to claim 1 wherein the metal utilized in the catalyst complex is rhodium.

6. A process according to claim 2 wherein the metal utilized in the catalyst complex is rhodium.

7. A process according to claim 3 wherein the metal utilized in the catalyst complex is rhodium.

8. A process according to claim 4 wherein the metal utilized in the catalyst complex is rhodium.

9. A hydrogenation process according to claim 1 wherein the compound being hydrogenated is represented by the formula

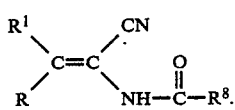

10. A hydrogenation process according to claim 2 wherein the compound being hydrogenated is represented by the formula

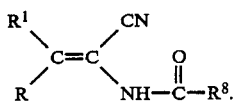

11. A hydrogenation process according to claim 3 wherein the compound being hydrogenated is represented by the formula

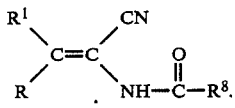

12. A hydrogenation process according to claim 4 wherein the compound being hydrogenated is represented by the formula

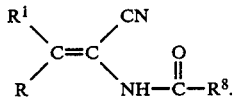

13. A hydrogenation process according to claim 5 wherein the compound being hydrogenated is represented by the formula

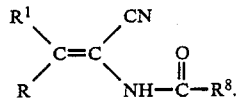

14. A hydrogenation process according to claim 1 wherein the compound being hydrogenated is (Z)-2-benzamido-3-phenyl-2-propenenitrile.

15. A hydrogenation process according to claim 1 wherein the compound being hydrogenated is

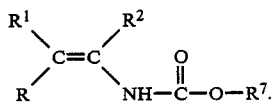

16. A hydrogenation process according to claim 2 wherein the compound being hydrogenated is

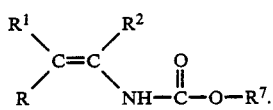

17. A hydrogenation process according to claim 3 wherein the compound being hydrogenated is

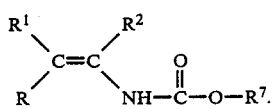

18. a hydrogenation process according to claim 4 wherein the compound being hydrogenated is

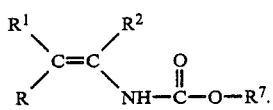

19. A hydrogenation process according to claim 5 wherein the compound being hydrogenated is

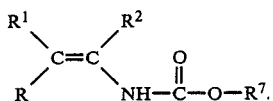

20. A hydrogenation process according to claim 1 wherein the compound being hydrogenated is (Z)-ethyl-2-ethyl-2-(N-ethoxycarbonylamino)-3-phenyl-2-propenoate.

* * * * *

UNITED STATES PATENT AND TRADEMARK OFFICE
CERTIFICATE OF CORRECTION

PATENT NO. : 4,515,731
DATED : May 7, 1985
INVENTOR(S) : Gerald L. Bachman et al It is certified that error appears in the above—identified patent and that said Letters Patent is hereby corrected as shown below:

Col. 2, footnote to formula at line 35 should end with "asymmetric"; and

"wherein R, $R^1$, $R^2$ and $R^3$ have the same meaning as described above" should be at beginning of next line.

Col. 8, line 6, should read -- A solution of 2.29 g. --.

Claim 20, line 3, should read -- ethyl-2-(N-ethoxycarbonyl-amino)-3-phenyl-2- --.

*Signed and Sealed this*

*Twentieth* Day of *August 1985*

[SEAL]

*Attest:*

DONALD J. QUIGG

*Attesting Officer*     *Acting Commissioner of Patents and Trademarks*